(12) United States Patent
Kozawa et al.

(10) Patent No.: US 8,960,027 B2
(45) Date of Patent: Feb. 24, 2015

(54) METHOD FOR CLASSIFYING POWDER

(75) Inventors: Kazumi Kozawa, Fujimino (JP);
Satoshi Akiyama, Fujimino (JP);
Kosuke Ando, Fujimi (JP)

(73) Assignee: Nisshin Engineering Inc., Tokyo (JP)

( * ) Notice: Subject to any disclaimer, the term of this patent is extended or adjusted under 35 U.S.C. 154(b) by 297 days.

(21) Appl. No.: 13/577,465

(22) PCT Filed: Apr. 23, 2010

(86) PCT No.: PCT/JP2010/057206
§ 371 (c)(1),
(2), (4) Date: Aug. 7, 2012

(87) PCT Pub. No.: WO2011/132301
PCT Pub. Date: Oct. 27, 2011

(65) Prior Publication Data
US 2012/0318042 A1    Dec. 20, 2012

(51) Int. Cl.
*B07B 4/02* (2006.01)
*B03B 1/02* (2006.01)
*B22F 1/00* (2006.01)
*G01N 15/02* (2006.01)
(Continued)

(52) U.S. Cl.
CPC ............... *B07B 4/02* (2013.01); *B22F 1/0085* (2013.01); *B07B 4/025* (2013.01); *G01N 15/02* (2013.01); *B22F 1/0081* (2013.01); *G01N 2033/0091* (2013.01); *G01N 15/042* (2013.01); *B07B 11/04* (2013.01); *B07B 7/086* (2013.01)
USPC ............................................ 73/865.5; 73/866

(58) Field of Classification Search
CPC .......... B07B 4/02; B07B 4/025; B07B 7/086; B07B 11/04; B07B 2220/00; B22F 1/0081; B22F 1/0085; B22F 2001/0092; G01N 15/02; G01N 15/042; G01N 2033/0091
USPC ...................................... 73/865.6, 866, 865.5
See application file for complete search history.

(56) References Cited

U.S. PATENT DOCUMENTS 2,833,665 A * 5/1958 Drexel et al. .................. 106/490
5,575,830 A * 11/1996 Yamashita et al. ......... B22F 1/00
(Continued)

FOREIGN PATENT DOCUMENTS

CA    2 493 827 A1    4/2006
CN    101357365 A     2/2009
(Continued)

OTHER PUBLICATIONS

International Preliminary Report on Patentability issued in International Application No. PCT/JP2010/057206 dated Nov. 6, 2012 (w/translation).
(Continued)

*Primary Examiner* — Thomas P Noland
(74) *Attorney, Agent, or Firm* — Oliff PLC

(57) ABSTRACT

Provided is a method for classifying a powder using a classifier, wherein the method comprises: a mixing step for mixing a powder and an auxiliary agent formed from an alcohol aqueous solution containing 10 to 50 mass % of an alcohol; an introduction step for introducing the powder mixed in the mixing step to the classifier; a heating step for heating a gas; a feed step for feeding the gas heated in the heating step to the classifier; and a classifying step for classifying the powder in the classifier on the basis of grain size.

2 Claims, 6 Drawing Sheets

(51) Int. Cl.
  *B07B 11/04* (2006.01)
  *B07B 7/086* (2006.01)
  *G01N 33/00* (2006.01)
  *G01N 15/04* (2006.01)

(56) References Cited

U.S. PATENT DOCUMENTS

| | | | |
|---|---|---|---|
| 6,872,251 B2 * | 3/2005 | Takaya et al. | 117/73 |
| 8,033,399 B2 | 10/2011 | Pistorius et al. | |
| 2006/0219056 A1 * | 10/2006 | Larink, Jr. | 75/338 |
| 2009/0032443 A1 | 2/2009 | Taketomi et al. | |
| 2009/0294333 A1 | 12/2009 | Pistorius et al. | |
| 2010/0270214 A1 | 10/2010 | Taketomi et al. | |
| 2011/0219854 A1 * | 9/2011 | Kozawa et al. | B07B 7/086 |

FOREIGN PATENT DOCUMENTS

| | | | | |
|---|---|---|---|---|
| EP | 2 351 620 A1 | | 8/2011 | |
| JP | 57144045 A | * | 9/1982 | B03C 1/30 |
| JP | 60260426 A | * | 12/1985 | 423/607 |
| JP | A-60-260426 | | 12/1985 | |
| JP | A-61-222562 | | 10/1986 | |
| JP | A-64-085149 | | 3/1989 | |
| JP | A-01-180285 | | 7/1989 | |
| JP | 03170323 A | * | 7/1991 | C01D 3/04 |
| JP | H0539687 U | * | 5/1993 | B07B 7/08 |
| JP | A-06-126252 | | 5/1994 | |
| JP | 10309530 A | * | 11/1998 | B07B 7/083 |
| JP | 2000157933 A | * | 6/2000 | B07B 7/08 |
| JP | 2006127872 A | * | 5/2006 | H01M 4/58 |
| JP | A-2009-034560 | | 2/2009 | |
| WO | WO 2008/034680 A1 | | 3/2008 | |
| WO | WO 2009/115933 A1 | | 9/2009 | |
| WO | WO 2010-047175 A1 | | 4/2010 | |

OTHER PUBLICATIONS

Mar. 5, 2014 Supplementary European Search Report issued in European Application No. 10 85 0242.
International Search Report issued in International Application No. PCT/JP2010/057206 dated Aug. 24, 2010.
Office Action issued in Japanese Application No. 2012-511484 dated Jul. 2, 2013 (with translation).
Office Action issued in Chinese Patent Application No. 201080062343 dated Apr. 28, 2014 (with translation).
Office Action issued in Korean Patent Application No. 2012-7020109 dated May 7, 2014 (with translation).

\* cited by examiner

METHOD FOR CLASSIFYING POWDER

TECHNICAL FIELD

The present invention relates to a method for classifying a powder, which realizes efficient classification of a powder having a particle size distribution in a desired classification point (grain size).

BACKGROUND ART

There has been known a classifying method in which a liquid auxiliary agent such as an alcohol is previously added when a powder such as glassy blast furnace slag is classified into a fine powder and a coarse powder (for example, see Patent Literature 1). In this classifying method, an auxiliary agent containing polar molecules is added to the powder to electrically neutralize the polarity of powder particles, and, thus, to prevent formation of aggregated particles with a large grain size due to adsorption and aggregation of the particles, whereby a decrease in classification efficiency is prevented.

CITATION LIST

Patent Literature

Patent Literature 1: Japanese Patent Application Laid-Open No. 64-85149

SUMMARY OF INVENTION

Technical Problem

Nowadays, with miniaturization and improvement of the performance of electronic materials, a battery and the like used in an electronic device, high accuracy classification of a raw material is required. However, when classification is performed using a conventional classification method, a powder of a raw material is adhered to each portion in a classifier to close an introduction port for the raw material and an injection port for a high-pressure gas, and therefore, the classification performance is degraded to lead to a difficulty of long periods of operation.

A problem of the present invention is to provide a method for classifying a powder, which realizes high accuracy classification of a powder.

Solution to Problem

A method for classifying a powder using a classifier according to the present invention includes the steps of: mixing a powder and an auxiliary agent formed from an alcohol aqueous solution containing 10 to 50 mass % of alcohol; introducing the powder mixed in the mixing step to the classifier; heating a gas; feeding the gas heated in the heating step to the classifier; and classifying the powder in the classifier on the basis of grain size.

Advantageous Effects of Invention

According to a method of classifying a powder according to the present invention, a powder can be classified with high accuracy, using an alcohol aqueous solution as an auxiliary agent.

DESCRIPTION OF EMBODIMENTS

Figure 1:
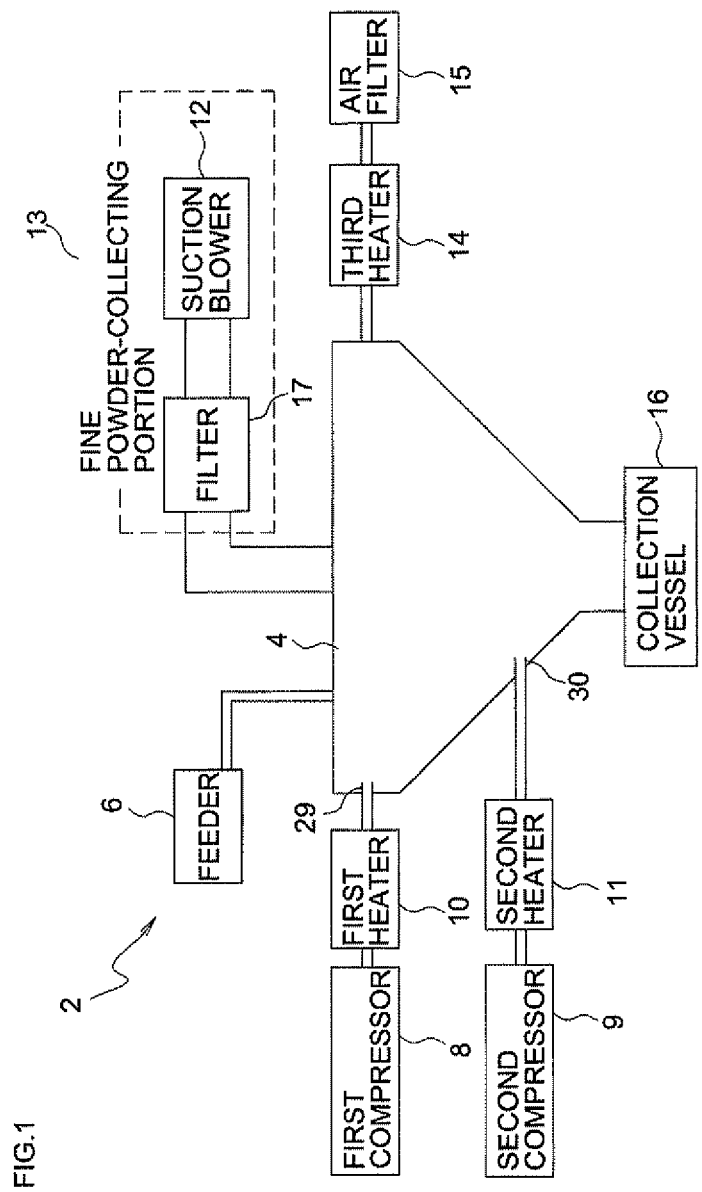
FIG. 1 is a schematic configuration diagram showing a configuration of a classification apparatus according to a first embodiment.

Hereinafter, a method for classifying a powder according to a first embodiment of the present invention will be described with reference to the drawings. FIG. 1 is a schematic configuration diagram showing a configuration of a classification apparatus used in the method for classifying a powder according to the first embodiment.

As shown in FIG. 1, a classifying apparatus 2 is provided with a classifier 4 which classifies a powder introduced as a raw material by a swirling airflow generated inside the classifying apparatus 2, a feeder 6 which introduces the powder in the classifier 4, a first air compressor 8 which feeds a high-pressure gas for dispersing a raw material to the classifier 4 through a first air nozzle (upper nozzle) 29, a first heater 10 which is disposed between the first air compressor 8 and the first air nozzle 29 and heats the high-pressure gas, fed from the first air compressor 8, to a predetermined temperature, a second air compressor 9 which feeds the high-pressure gas for enhancing the effects of a centrifugal separation action to the classifier 4 through a second air nozzle (lower nozzle) 30, and a second heater 11 which is disposed between the second air compressor 9 and the second air nozzle 30 and heats the high-pressure gas, fed from the second air compressor 9, to a predetermined temperature. The classifying apparatus 2 further has a fine powder-collecting portion 13 which suctions a fine powder, separated to not more than a desired classification point, along with a gas in the classifier 4 through a fine powder inlet 32 (see, FIG. 2) provided in an upper portion of the classifier 4 and collects the fine powder, an air filter 15 which removes dusts in the atmosphere (gas at normal pressures) suctioned from around the classifier 4, using a negative pressure generated in the classifier 4, a third heater 14 which heats the atmosphere (gas at normal pressures) passed through the air filter 15, and a collection vessel 16 which is disposed under the classifier 4 and collects a centrifugally separated coarse powder with a large grain size. The fine powder-collecting portion 13 is provided with a suction blower 12 which suctions a gas in the classifier 4 and a filter 17 which is disposed between the fine powder inlet 32 and the suction blower 12 and collects a fine powder from a gas passed through the fine powder inlet 32.

The classifier 4 has a substantially conical shape and is installed so that the apex of the cone faces downward. The upper portion of the classifier 4 has a centrifugal separation chamber 20 (see, FIG. 2) to be described later in detail. A powder to be classified is introduced into the centrifugal separation chamber 20 from the feeder 6.

The feeder 6 includes a screw (not shown). A powder stored in the feeder 6 can be delivered quantitatively by rotating the screw. The powder thus sent is introduced in the classifier 4 through an introduction port 26 (see, FIG. 2) provided on the top surface of the classifier 4. The powder stored in the feeder 6 is previously mixed with an auxiliary agent using a method to be described later.

The first air compressor 8 compresses the atmosphere to produce a high-pressure gas, and, thus, to feed the high-pressure gas into the classifier 4 through the first heater 10. The second air compressor 9 compresses the atmosphere to produce a high-pressure gas, and, thus, to feed the high-pressure gas into the classifier 4 through the second heater 11.

The first heater 10 and the second heater 11 include piping through which a high-pressure gas is passed, and heating means constituted of filaments, aerofins and the like is installed the piping. The heating means heats the high-pressure gas passed through the piping to a predetermined temperature and at the same time removes moisture contained in the high-pressure gas. Different dehydration means that removes moisture contained in the high-pressure gas may be separately provided between the first air compressor 8 and the classifier 4 and between the second air compressor 9 and the classifier 4, or a filter which removes dusts and the like may be suitably provided.

The suction blower 12 suctions a fine powder separated by the classifier 4 along with a gas existing in the classifier 4 through the fine powder inlet 32 (see, FIG. 2) provided at the center of the top surface of the classifier 4, and the fine powder is collected by a filter 17 provided between the fine powder inlet 32 and the suction blower 12. When the suction blower 12 suctions a gas, a negative pressure is generated in the classifier 4, and therefore, the atmosphere as a gas at normal pressures existing outside the classifier 4 is suctioned into the classifier 4 through the air filter 15 and the third heater 14. By virtue of the suction of the gas at normal pressures, a swirling airflow swirling at high speed is formed in the centrifugal separation chamber 20 of the classifier 4. Since the classifying apparatus 2 according to this embodiment is provided with the air filter 15, dusts and the like in the atmosphere can be prevented from entering inside the centrifugal separation chamber 20. Since the classifying apparatus 2 is further provided with the third heater 14 which heats a suctioned gas at normal pressures, a temperature of the swirling airflow in the centrifugal separation chamber 20 can be heated to a predetermined temperature. The third heater 14 includes piping through which a gas at normal pressures is passed as with the first heater 10 and the second heater 11, and heating means such as filaments and aerofins is installed in the piping.

The collection vessel 16 is installed at the lowermost portion of the classifier 4 and collects a coarse powder, which is centrifugally separated in the centrifugal separation chamber 20 and then moves down along the slope of the cone-shaped portion of the classifier 4.

Figure 2:
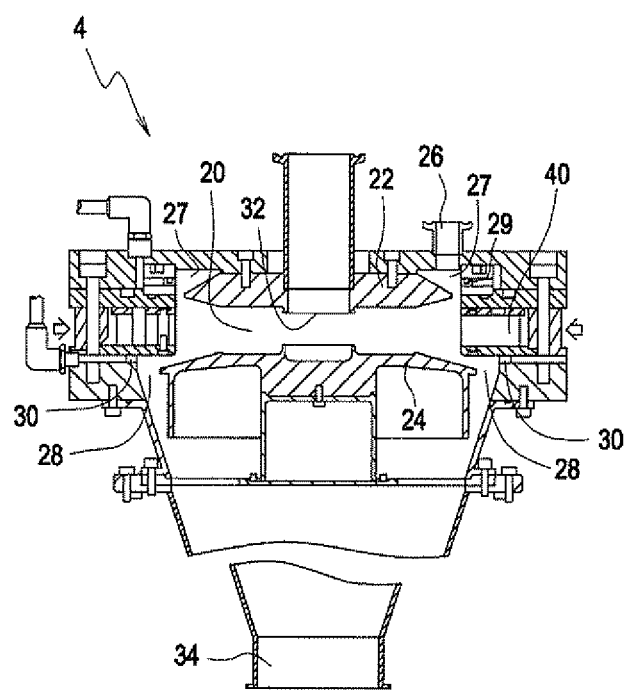
FIG. 2 is a longitudinal cross-sectional view showing a configuration of an inside of a classifier according to the first embodiment.
Figure 3:
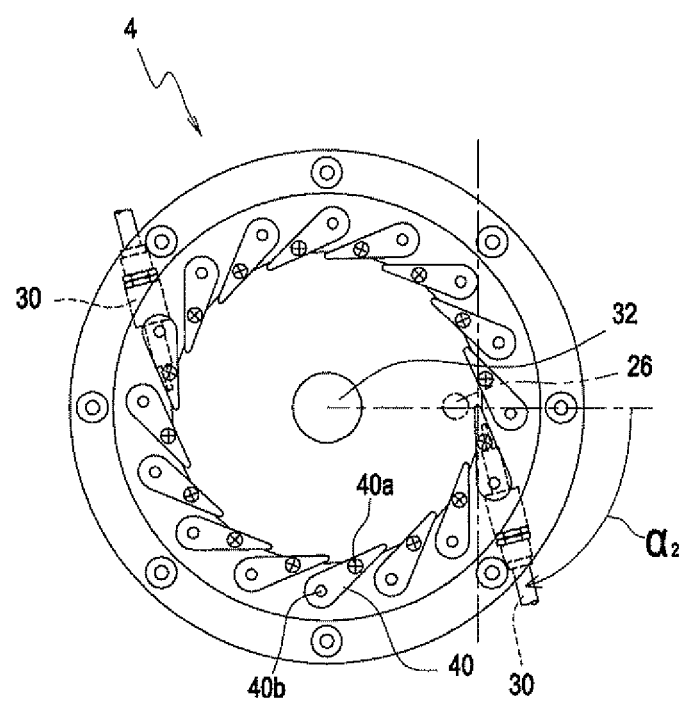
FIG. 3 is a lateral cross-sectional view showing the configuration of the inside of the classifier according to the first embodiment.

Next, the classifier 4 according to the embodiment will be described with reference to FIGS. 2 and 3. FIG. 2 is a longitudinal cross-sectional view according to a surface including the central axis of the classifier 4. FIG. 3 is a lateral cross-sectional view at the position of the centrifugal separation chamber 20 according to a plane vertical to the central axis. In order to clarify the relative positional relationship with other components (in particular, the second air nozzle 30 and a guide vane 40 to be described later), the introduction port 26 and the second air nozzle 30 not normally illustrated in FIG. 3 are shown respectively by a virtual line and a dotted line. Only the two second air nozzles 30 are illustrated for the purposes of description.

As shown in FIG. 2, an upper disk-shaped member 22 having a flat disk shape and a lower disk-shaped member 24 having a hollow disk shape are arranged in the upper portion of the classifier 4 while keeping a predetermined interval there between, and the centrifugal separation chamber 20 having a columnar shape is formed between both the disk-shaped members. The introduction port 26 through which a powder introduced from the feeder 6 is passed is provided above the centrifugal separation chamber 20, and a raw material dispersion zone 27 is formed into a donut shape along an outer peripheral wall of the upper disk-shaped member 22. As shown in FIG. 3, a plurality of the guide vanes 40 are arranged at regular intervals on the outer periphery of the centrifugal separation chamber 20, and a reclassification zone 28 where a powder centrifugally separated and then moving down from the centrifugal separation chamber 20 is jetted and returned into the centrifugal separation chamber 20 is formed into a donut shape along an outer peripheral wall of the lower disk-shaped member 24 in the lower portion of the centrifugal separation chamber 20.

A first air nozzle 29 jetting a high-pressure gas for dispersing a raw material fed from the first air compressor 8 is disposed on an outer peripheral wall of the raw material dispersion zone 27. The first air nozzle 29 is disposed so that the jetting direction is substantially the same as the tangential direction of the outer peripheral wall of the raw material dispersion zone 27.

A second air nozzle 30 jetting a high-pressure gas which is fed from the second air compressor 9 and used for enhancing the effects of a centrifugal separation action is disposed near an upper end of the outer peripheral wall of the reclassification zone 28. The second air nozzle 30 is disposed so that the jetting direction is substantially the same as the tangential direction of the outer peripheral wall of the reclassification zone 28.

The second air nozzle 30 jets a high-pressure gas to disperse a powder introduced through the introduction port 26 and at the same time supplementarily feeds a gas into the centrifugal separation chamber 20. Further, the second air nozzle 30 jets and returns a fine powder existing in the reclassification zone 28 into the centrifugal separation chamber 20. In the present embodiment, although six second air nozzles 30 are arranged on the outer peripheral wall of the reclassification zone 28, this is only an example, and it is possible to freely determine the arrangement location and the number of the second air nozzles 30.

As shown in FIG. 3, a second nozzle angle of the second air nozzle 30 can be represented by an inclination angle $\alpha_2$ with respect to the vertical direction of the tangent of the outer peripheral wall of the reclassification zone 28, and the inclination angle $\alpha_2$ can be suitably changed.

Similarly, the nozzle angle of the first air nozzle 29 can be represented by an inclination angle $\alpha_1$ with respect to the vertical direction of the tangent of the outer peripheral wall of the raw material dispersion zone 27, and the inclination angle $\alpha_1$ is preferably within a range of 45° to 90°. When the inclination angle $\alpha_1$ is within this range, a great effect can be obtained in that a fine powder to be separated in the direction of the fine powder inlet 32 is prevented from being mixed with a coarse powder and separated in the direction of the collection vessel 16 through an outlet 34.

The fine powder inlet 32 through which a fine powder separated from a coarse powder by centrifugal separation is suctioned and collected is installed at the center of the upper portion of the centrifugal separation chamber 20. The centrifugally separated coarse powder moves down the slope of the cone-shaped portion of the classifier 4 from the reclassification zone 28 to be discharged from the outlet 34 installed at the lowermost portion of the classifier 4, and, thus, to be stored in the collection vessel 16.

The guide vane 40 forms a swirling airflow in the centrifugal separation chamber 20 and at the same time adjusts the swirling speed of the swirling airflow. In this embodiment, sixteen guide vanes 40 are arranged as an example. The guide vane 40 is rotatably pivotally supported by a rotation shaft 40a between the upper disk-shaped member 22 and the lower disk-shaped member 24 and at the same time anchored to a rotating board (rotating means) (not shown) through a pin 40b. All the guide vanes 40 can be simultaneously rotated by a predetermined angle by rotating the rotating board. The guide vane 40 is thus rotated by the predetermined angle to adjust the angle and interval of each of the guide vanes 40, whereby the flow rate of a gas at normal pressures passed in the direction of the hollow arrow shown in FIG. 2 can be changed, and, furthermore, the flow rate of the swirling airflow inside the centrifugal separation chamber 20 can be changed. The flow rate of the swirling airflow is thus changed, whereby the classification performance (specifically, the classification point) of the classifier 4 according to the present embodiment can be changed. As described above, the gas at normal pressures passed through each interval of the guide vanes 40 is a gas at normal pressures previously heated to a predetermined temperature by the third heater 14.

Next, a method for classifying a powder according to this embodiment will be described using a flowchart shown in FIG. 4. First, a powder to be classified and an auxiliary agent as a liquid are mixed (step S10). Although the kind of the auxiliary agent to be used may be suitably selected according to the kind of a powder to be classified, an alcohol aqueous solution is preferably used, for example. For example, ethanol can be used as alcohol. The alcohol concentration in the alcohol aqueous solution is preferably 10 to 50 mass %.

Although the amount of adding an auxiliary agent and the mixing method may be suitably selected according to the kind of a powder, in the method of classifying a powder according to the present embodiment, an auxiliary agent with a predetermined ratio is added to a powder to be classified and then mixed using a mixer. A Hi-X 200 (manufactured by Nissin Engineering Inc.) is used as the mixer, and an optimum rotation speed of an impeller and an optimum rotation speed of a scraper are selected according to the kind of the powder to be classified and an auxiliary agent to be used. The amount of a powder to be classified, which is mixed in the mixer, is suitably selected. Since the auxiliary agent added to a powder is partially evaporated during mixed with the powder and after the mixing, when a mixed powder is introduced into the feeder 6 of the classifying apparatus 2, the amount of the auxiliary agent contained in the mixed powder may be reduced to less than the amount of the auxiliary agent added at the start of mixing.

When the operation of the classifying apparatus 2 is started, the suction of a gas is started by the suction blower 12 (step S12). Since the gas inside the centrifugal separation chamber 20 is suctioned from the fine powder inlet 32 provided at the center of the upper portion of the centrifugal separation chamber 20, the air pressure at the center of the centrifugal separation chamber 20 becomes relatively low. In this way, due to the negative pressure generated in the centrifugal separation chamber 20, the atmosphere which is a gas at normal pressures previously heated to a predetermined temperature (step S14) passes through the piping, provided in the third heater 14, from between the guide vanes 40 arranged along the outer circumference of the centrifugal separation chamber 20 to be suctioned, and, thus, to be fed in the centrifugal separation chamber 20 (step S16). When the gas at normal pressures is suctioned from between the guide vanes 40 in this way, a swirling airflow having the flow rate determined according the rotation angle of the guide vane 40 is formed. In the method for classifying a powder according to this embodiment, the gas at normal pressures to be suctioned is heated so that the temperature of the swirling airflow in the centrifugal separation chamber 20 is approximately 100° C.

Next, the feeding of a high-pressure gas to the inside of the centrifugal separation chamber 20 of the classifier 4 is started using the first air compressor 8 and the second air compressor 9. The high-pressure gas jetted from the first air compressor 8 and the second air compressor 9 is heated to a predetermined temperature by the first heater 10 and the second heater 11 (step S18). As with the third heater 14, the first heater 10 and the second heater 11 heat the high-pressure gas so that the temperature of the swirling airflow in the centrifugal separation chamber 20 is approximately 100° C. The high-pressure gas heated to the predetermined temperature is jetted from a plurality of the first air nozzles 29 and a plurality of the second air nozzles 30 provided on the outer peripheral wall of the centrifugal separation chamber 20 and fed into the centrifugal separation chamber 20 (step S20).

As described above, when such a state is formed that the high-speed swirling airflow heated to approximately 100° C. swirls steadily in the centrifugal separation chamber 20, the mixed powder delivered quantitatively from the feeder 6 is introduced into the centrifugal separation chamber 20 through the introduction port 26 (step S22). As shown in FIG. 2, since the introduction port 26 is provided on the upper side of the outer circumference of the centrifugal separation chamber 20, the mixed powder introduced from the introduction port 26 collides with the swirling airflow swirling at high speed in the centrifugal separation chamber 20 and is dispersed rapidly. At this time, the auxiliary agent mixed in between fine particles of the powder is vaporized rapidly to promote dispersion of the powder. The powder thus dispersed in units of fine particles swirls countless times in the centrifugal separation chamber 20 without adhering onto the surface of the upper disk-shaped member 22, the lower disk-shaped member 24 and the like constituting the centrifugal separation chamber 20 and is classified on the basis of the grain size of the powder (step S24).

As a result of the centrifugal separation action in the centrifugal separation chamber 20, a fine powder having a grain size of not more than a desired classification point is aggregated in the center of the centrifugal separation chamber 20 and collected from the fine powder inlet 32 along with a gas suctioned by the suction blower 12 due to the effects of ring-shaped protrusions provided in the respective centers of the upper disk-shaped member 22 and the lower disk-shaped member 24 (step S26). A rough powder having a grain size exceeding the classification point is aggregated in the outer circumference in the centrifugal separation chamber 20 by the centrifugation separation action in the centrifugal separation chamber 20 to then move down the conical-shaped portion of the classifier 4 from the reclassification zone 28, and, thus, to be discharged from the outlet 34, whereby the rough powder is collected in the collection vessel 16.

As described above, a powder dispersed efficiently by the effects of the high-temperature swirling airflow swirling in the centrifugal separation chamber 20 and the auxiliary agent swirls in the centrifugal separation chamber 20 without adhering to the surfaces of the components and the like constituting the centrifugal separation chamber 20 and is classified efficiently into the fine powder of not mare than a desired classification point and the remaining rough powder. Since the added auxiliary agent is all vaporized, no auxiliary agent is contained in a collected powder.

In this embodiment, although the fed gas is heated so that the temperature of the swirling airflow in the classifier 4 is approximately 100° C., the temperature of the swirling airflow in the classifier 4 is not limited to approximately 100° C., and the temperature at which the auxiliary agent is vaporized in the centrifugal separation chamber 20 may be employed.

Next, a method for classifying a powder according to a second embodiment of the present invention will be described with reference to the drawings. In the configuration of the method for classifying a powder according to the second embodiment, the mixing process in the method for classifying a powder according to the first embodiment is changed so that mixing is performed while heating. Accordingly, a detailed description of the same configuration as the above classifying apparatus 2 is omitted, and only different portions will be described in detail. The same components as those of the classifying apparatus 2 are assigned the same reference numerals in the following description.

Figure 5:
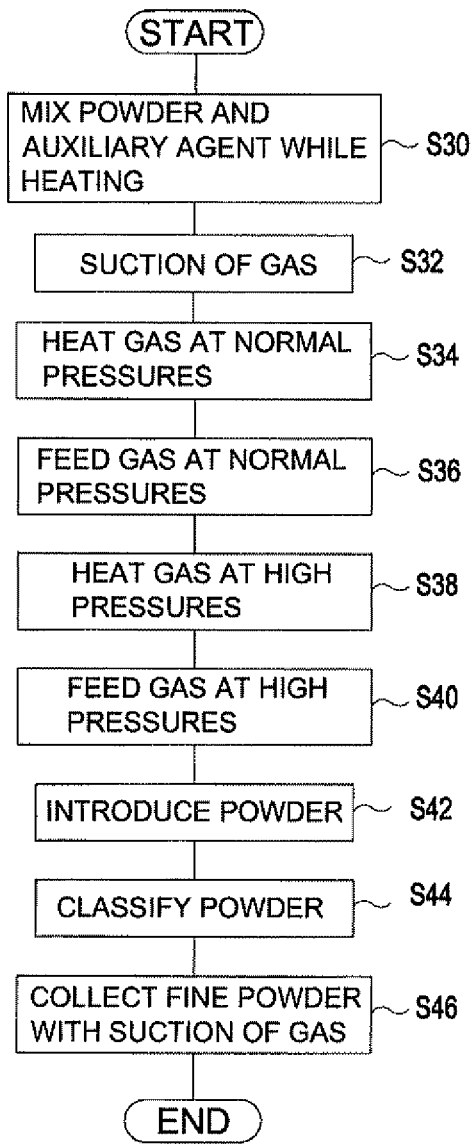
FIG. 5 is a flowchart for explaining a method for classifying a powder, according to a second embodiment.

FIG. 5 is a flowchart for explaining the method for classifying a powder according to the second embodiment. First of all, a powder to be classified and an auxiliary agent are mixed in a mixer while being heated (step S30). The kind of the auxiliary agent to be used may be suitably selected according to the kind of the powder to be classified, and an alcohol aqueous solution is preferably used, for example. As alcohol, ethanol may be used, for example. The alcohol concentration in the alcohol aqueous solution is preferably 10 to 50 mass %.

Figure 4:
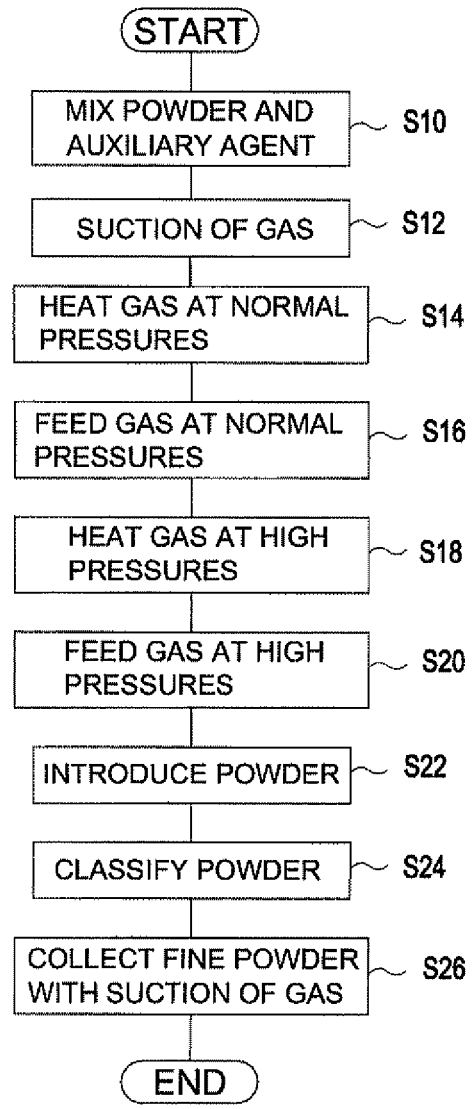
FIG. 4 is a flowchart for explaining a method for classifying a powder, according to the first embodiment.

Next, although processings shown in steps S32 to S40 are performed, these processings are similar to processings shown in steps S12 to 920 of the flowchart of FIG. 4, and the description will be omitted. A mixed powder delivered quantitatively from the feeder 6 is introduced into the centrifugal separation chamber 20 through the introduction port 26 (step S42). At this time, the mixed powder heated in step S30 is introduced into the centrifugal separation chamber 20 at a predetermined temperature. Then, the processings shown in steps S44 and S46 are performed. Since these processings are similar to the processings shown in steps S24 and S26 of the flowchart of FIG. 4, the description will be omitted.

With regard to setting of the temperature of the swirling airflow in the centrifugal separation chamber 20, for example, a suctioned gas at normal pressures is heated by the third heater 14 in step S34 so that the temperature of the swirling airflow is approximately 100° C., and the high-pressure gas is similarly heated by the first heater 10 and the second heater 11 in step S40 so that the temperature of the swirling airflow is approximately 100° C.

Example

Next, the method for classifying a powder according to the present embodiment will be described more specifically using an example.

(Mixing of Powder and Auxiliary Agent)

A Kanto roam burned product (JIS Z 8901 Powder for test 1-11, D50 (median diameter)=2.7 μm, ratio not more than 1 μm=50.2 pop %) was used as a powder, and an auxiliary agent of 8 mass % was added to the powder. 10 to 50 mass % of an ethanol aqueous solution was used as the auxiliary agent.

The powder containing the auxiliary agent was injected into a mixer (Hi-X 200: manufactured by Nissin Engineering Inc.) and mixed. The mixer was set so that the impeller rotation speed was 3000 rotations/min, the scraper rotation speed was 45 rotations/min, and the temperature in the mixer was 80° C. 500 g of the powder was used for one mixing operation.

(Classification of Powder)

A mixture of the auxiliary agent with the powder obtained by the mixer was classified using a classifier.

In this example, a classifier (Aerofine Classifier AC-20: manufactured by Nissin Engineering Inc.) in which a heat insulating equipment is provided was used. The amount of a gas suctioned by the suction blower 12 shown in FIG. 1 was 2 m$^3$/min, and pressure was 20 to 50 kPa. The amount of the gas suctioned by the suction blower 12 corresponds to the amount of a gas at normal pressures suctioned from between the guide vanes 40. The angle of the guide vane 40 was 90° (tangential direction).

The conditions of a high-pressure gas jetted through the second air nozzle 30 were fixed so that the pressure was 0.5 MPa and the gas volume was 215 NL (normal liter)/min. The nozzle bore diameter φ of the second air nozzle 30 is 0.8 mm, and six second air nozzles 30 are provided at regular intervals on the outer peripheral wall of the reclassification zone 28. The nozzle angle ($\alpha_2$) was 75°.

The conditions of a high-pressure gas jetted through the first air nozzle 29 were changed within a range where the pressure was 0.2 to 0.6 MPa and the gas volume was 390 to 560 NL/min, and classification was performed. The first air nozzle 29 has a nozzle bore diameter of 1.3 mm, and six first air nozzles 29 are provided at regular intervals on the outer peripheral wall of the raw material dispersion zone 27. The nozzle angle ($\alpha_1$) was 75°. Further, introduction of a mixture of a powder as a raw material with an auxiliary agent into a classifier was set to 1 kg/hour.

Figure 6:
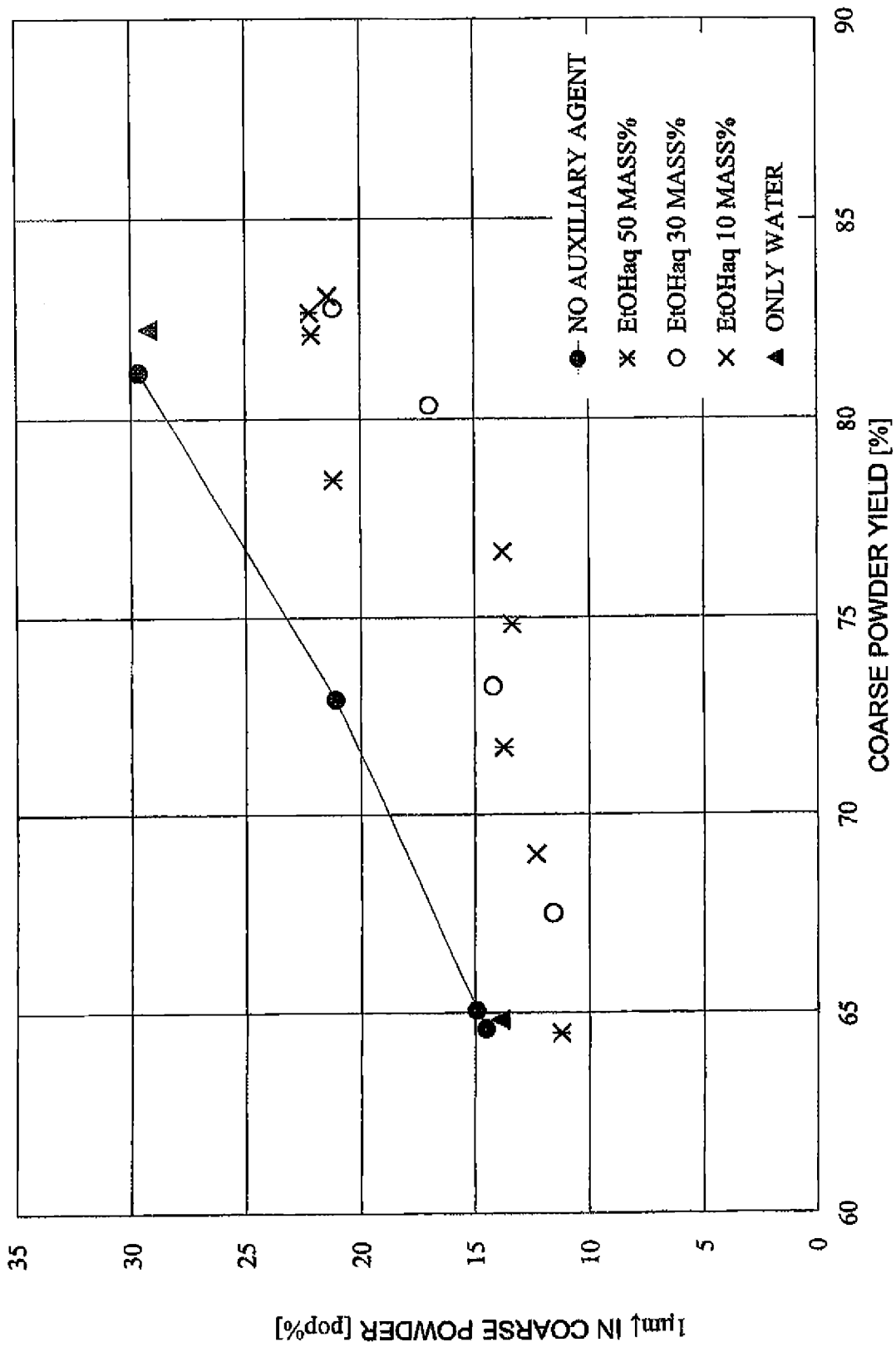
FIG. 6 is a graph showing results of an example.

After the classification, a coarse powder collected in the collection vessel 16 was analyzed, and the results shown in FIG. 6 were obtained. FIG. 6 shows the results in an example using ethanol aqueous solutions as the auxiliary agents, whose ethanol concentrations are respectively 10 mass %, 30 mass %, and 50 mass %, a comparative example not using the auxiliary agent, and a comparative example using water as the auxiliary agent.

In the vertical axis of the graph shown in FIG. 6, a ratio of the number of particles of not more than 1 μm of 50,000 measured particles is represented as "pop %". Namely, the ratio of the number of particles (fine powder) of not more than 1 μm contained in a coarse powder is shown. In the horizontal axis shown in FIG. 6, the yield (%) of the coarse powder relative to an introduced powder is shown. In this graph, when the yield of the coarse powder is the same, the smaller the ratio of the number of the particles of not more than 1 μm in the coarse powder, the better the classification performance.

According to the results shown in the graph of FIG. 6, more excellent classification performance is obtained when the ethanol aqueous solution containing 10 to 50 mass % of ethanol as an auxiliary agent is used than when the auxiliary agent is not used and when water is used as the auxiliary agent.

REFERENCE SIGNS LIST

2 Classifying apparatus
4 Classifier
6 Feeder
8 First air compressor
9 Second air compressor
10 First heater
11 Second heater
12 Suction blower
14 Third heater
16 Collection vessel
20 Centrifugal separation chamber
22 Upper disk-shaped member
24 Lower disk-shaped member
26 Introduction port
29 First air nozzle
30 Second air nozzle
32 Fine powder inlet 34 Outlet
40 Guide vane

The invention claimed is:

1. A method for classifying a powder using a classifier comprising the steps of:
   mixing a powder and an auxiliary agent formed from an alcohol aqueous solution containing 10 to 50 mass % of alcohol;
   introducing the powder mixed in the mixing step to the classifier;
   heating a gas;
   feeding the gas heated in the heating step to the classifier; and
   classifying the powder in the classifier on the basis of grain size.

2. The method for classifying a powder according to claim 1, wherein the alcohol is ethanol.

* * * * *